United States Patent [19]

Ondetti et al.

[11] 4,140,864
[45] Feb. 20, 1979

[54] SUBSTITUTED ACYL DERIVATIVES OF AMINO ACIDS

[75] Inventors: Miguel A. Ondetti, Princeton; Frank L. Weisenborn, Titusville, both of N.J.

[73] Assignee: E. R. Squibb & Sons, Inc., Princeton, N.J.

[21] Appl. No.: 889,768

[22] Filed: Mar. 24, 1978

Related U.S. Application Data

[62] Division of Ser. No. 747,280, Dec. 3, 1976.

[51] Int. Cl.² ............... C07C 153/07; C07C 149/243; A61K 31/265; A61K 31/195
[52] U.S. Cl. ...................... 562/426; 546/245; 260/326.12 R; 260/326.2; 260/326.48; 260/327 S; 424/267; 424/273 R; 424/274; 424/277; 424/301; 424/309; 424/311; 424/319; 548/342; 548/344; 560/16; 560/147; 560/250; 562/542; 562/556; 562/557; 562/581
[58] Field of Search ............. 260/516, 455 R; 560/16, 560/147, 250

[56] References Cited

U.S. PATENT DOCUMENTS

| | | | |
|---|---|---|---|
| 2,714,119 | 7/1955 | Crounse | 260/561 |
| 3,510,504 | 5/1970 | Gerzon | 260/471 |
| 3,624,143 | 11/1971 | Shen | 260/516 |
| 3,835,149 | 9/1974 | Renfroe | 260/297 |
| 3,971,828 | 7/1976 | Mita | 260/516 |
| 4,046,889 | 9/1977 | Ondetti | 260/293.73 |
| 4,053,651 | 10/1977 | Ondetti | 260/516 |

Primary Examiner—James O. Thomas, Jr.
Assistant Examiner—Michael Shippen
Attorney, Agent, or Firm—Lawrence S. Levinson; Merle J. Smith

[57] ABSTRACT

New substituted acyl derivatives of amino acids which have the general formula

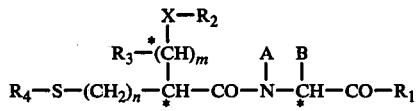

are useful as angiotensin converting enzyme inhibitors.

11 Claims, No Drawings

SUBSTITUTED ACYL DERIVATIVES OF AMINO ACIDS

This is a division of application Ser. No. 747,280, filed Dec. 3, 1976.

SUMMARY OF THE INVENTION

This invention relates to new substituted acyl derivatives of amino acids which have the general formula

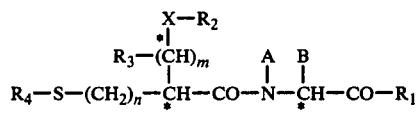

and salts thereof, wherein $R_1$ is hydroxy or lower alkoxy;
$R_2$ is hydrogen, lower alkyl or lower alkanoyl;
$R_3$ is hydrogen or lower alkyl;
$R_4$ is hydrogen, lower alkanoyl, benzoyl or

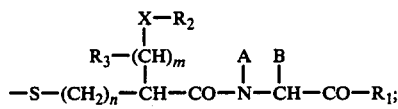

A is hydrogen, lower alkyl or hydroxy-lower alkylene;

B is hydrogen, lower alkyl, phenyl, phenyl-lower alkylene, hydroxy-lower alkylene, hydroxyphenyl-lower alkylene, amino-lower alkylene, guanidino-lower alkylene, mercapto-lower alkylene, lower alkyl-mercapto-lower alkylene, imidazolyl-lower alkylene, indolyl-lower alkylene, carbamoyl-lower alkylene or carboxy-lower alkylene;

or A and B together form a $(CH_2)_p$ bridge which completes a ring of 5 or 6 atoms with the nitrogen and carbon to which they are joined, one carbon optionally bearing a hydroxy group;

X is oxygen or sulfur;
n is 0 or 1;
m is 0, 1, 2, 3 or 4; and
p is 3 or 4.

The asterisks denote centers of asymmetry.

DETAILED DESCRIPTION OF THE INVENTION

The invention in its broad aspects includes substituted acyl derivatives of amino acids having formula I above. The substituted acyl groups refer to the side chains on the carbon beta to the nitrogen atom. The one side chain has one or two sulfur containing groups and the second side chain has one oxygen or sulfur containing group. Within the class defined by formula I, because of their properties, certain subgroups are preferred.

Compounds in the group represented by formula I which are derived from or include the structure of the amino acids glycine, alanine, leucine, threonine, phenylalanine, lysine, arginine, glutamine, histidine, methionine, serine, cysteine, tyrosine, valine, asparagine, glutamic acid, proline, hydroxyproline, phenylglycine or tryptophane are broadly preferred. Preferred modifications are compounds of formula I wherein $R_1$ is hydroxy; $R_2$ is hydrogen, lower alkyl or lower alkanoyl (particularly hydrogen, methyl or acetyl); $R_3$ is hydrogen or lower alkyl (particularly hydrogen or methyl); $R_4$ is hydrogen, lower alkanoyl or benzoyl (particularly hydrogen, or acetyl); X is oxygen or sulfur; A is hydrogen; B is lower alkyl, guanidino-lower alkylene (particularly guanidinopropyl), amino-lower alkylene (particularly amino-$C_3$-$C_4$-lower alkylene) or phenyl-lower alkylene(particularly phenylmethyl);or A and B complete a 5- or 6-membered ring; m is 0 or 1 and n is 0 or 1. There is only one alkyl substituent $R_3$.

Especially preferred are those compounds of formula I which are derived from proline and have the formula

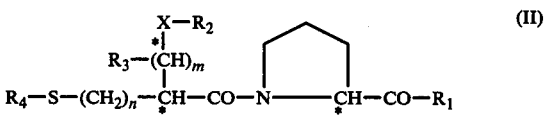

The symbols have the same preferred meanings described above.

The lower alkyl groups represented by any of the variables include straight and branched chain hydrocarbon radicals from methyl to heptyl, for example, methyl, ethyl, propyl, isopropyl, butyl, isobutyl, t-butyl, pentyl, isopentyl and the like. The lower alkylene groups are of the same kind also having 1 to 7 carbons. Similarly, the lower alkoxy groups are of the same kind with a link to oxygen, for example, methoxy, ethoxy, propoxy, isopropoxy, butoxy, isobutoxy, t-butoxy and the like. The $C_1$-$C_4$ members, especially $C_1$ and $C_2$ members, of all types are preferred. Phenylmethyl is the preferred phenyl-lower alkylene group and methoxy and t-butoxy the preferred lower alkoxy groups. The lower alkanoyl groups are the acyl radicals of the lower (up to 7 carbons) fatty acids, e.g., acetyl, propionyl, butyryl and the like, acetyl being preferred.

The products of formula I and the preferred subgroups can be produced by various methods of synthesis. According to a preferred method, the amino acid of the formula

wherein A, B and $R_1$ are defined as above, is acylated with an acid of the formula

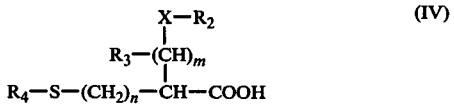

wherein $R_2$, $R_3$, $R_4$, X, m and n have the meaning defined above, by one of the known procedures in which the acid IV is activated, prior to reaction with the amino acid III, involving formation of a mixed anhydride, symmetrical anhydride, acid chloride, active ester, Woodward reagent K, N,N'-carbonylbisimidazole, EEDQ (N-ethoxycarbonyl-2-ethoxy-1,2-dihydroquinoline) or the like. [For a review of these methods, see Methoden der Organischen Chemie (Houben-Weyl) Vol. XV, parts 1 and 2 (1974)].

When the product obtained is an ester, e.g., $R_1$ is t-butoxy, the ester can be converted to the free carboxy group by treatment with trifluoroacetic acid and anisole, then with a base like sodium bicarbonate. Conversely the free acid can be esterified by conventional procedures.

The acids of formula IV wherein n is 1 can be synthesized by several procedures. The preferred method is the addition of thiolacetic acid to the substituted acrylic acid of the formula

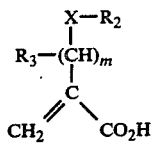
(V)

When n is 0, the acids of formula IV are synthesized by the reaction of an α-halo derivative of the formula

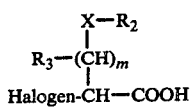
(VI)

with a thiolacetic acid or thiobenzoic acid to give the acid of the formula

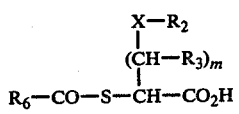
(VII)

wherein $R_6$ is lower alkyl, preferably methyl or phenyl.

An alternate procedure for the synthesis of compounds of formula I wherein n is 0, is the acylation of the amino acid III with the acid of formula VI followed by displacement with thiolacetic acid or thiobenzoic acid.

The disulfides of formula I, wherein $R_4$ is

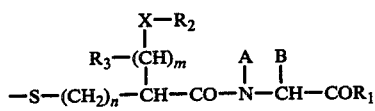

are obtained by oxidation of the compound of the formula

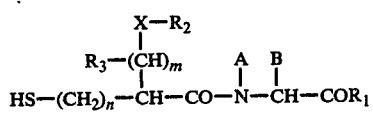
(VIII)

e.g., with an alcoholic solution of iodine.

Another alternate method for the production of acids of formula IV is the reaction of a halo derivative of the formula

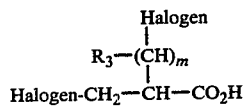
(IX)

or the formula

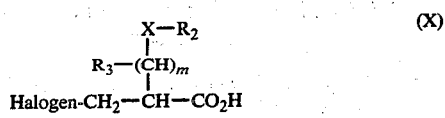
(X)

with thiolacetic acid or p-methoxybenzylmercaptan to give a compound of the formula

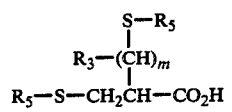
(XI)

or the formula

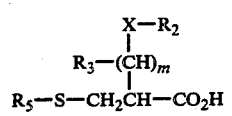
(XII)

respectively, wherein $R_5$ is lower alkanoyl, e.g., acetyl, or

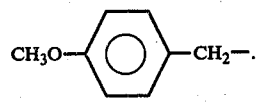

After coupling of the acids XI or XII to the amino acid III, the lower alkanoyl group is removed by ammonolysis, e.g., with concentrated ammonia, and the

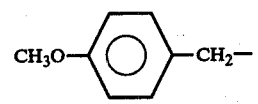

group is removed by acidolysis, e.g., with trifluoromethanesulfonic acid.

Also included in the invention are intramolecular disulfides wherein the two sulfur atoms, when X is sulfur, join in a dithiolane ring. These have the formula

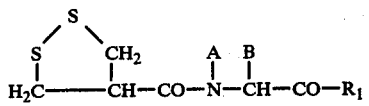
(XIII)

wherein $R_1$, A and B have the same meaning as defined previously. Such compounds are produced by acylating III with 1,2-dithiolane-4- carboxylic acid as described above.

Products of formula I have two or three asymmetric carbon atoms. These carbon atoms are indicated by an asterisk in formula I. The compounds accordingly exist in diastereoisomeric forms or in racemic mixtures thereof. All of these are within the scope of the invention. The above described syntheses can utilize the racemate or one of the enantiomers as starting material. When the racemic starting material is used in the synthetic procedure, the stereoisomers obtained in the product can be separated by conventional chromatographic or fractional crystallization methods. In general, the L-isomer with respect to the carbon of the amino acid constitutes the preferred isomeric form.

The compounds of this invention form basic salts with various inorganic and organic bases which are also within the scope of the invention. Such salts include ammonium salts, alkali metal salts like sodium and potassium salts (which are preferred), alkaline earth metal salts like the calcium and magnesium salts, salts with organic bases, e.g., dicyclohexylamine salt, benzathine, N-methyl-D-glucamine, hydrabamine salts, salts with amino acids like arginine, lysine and the like. The nontoxic, physiologically acceptable salts are preferred, although other salts are also useful, e.g., in isolating or purifying the product.

The salts are formed in conventional manner by reacting the free acid form of the product with one or more equivalents of the appropriate base providing the desired cation in a solvent or medium in which the salt is insoluble, or in water and removing the water by freeze drying. By neutralizing the salt with an insoluble acid like a cation exchange resin in the hydrogen form [e.g., polystyrene sulfonic acid resin — Dowex 50 (Mikes, Laboratory Handbook of Chromatographic Methods (Van Nostrand, 1961) page 256] or with an aqueous acid and extraction with an organic solvent, e.g., ethyl acetate,, dichloromethane or the like, the free acid form can be obtained, and, if desired, another salt formed.

Additional experimental details are found in the examples which are preferred embodiments and also serve as models for the preparation of other members of the group.

The compounds of this invention inhibit the conversion of the decapeptide angiotensin I to angiotensin II and therefore are useful in reducing or relieving angiotensin related hypertension. The action of the enzyme renin on angiotensinogen, a pseudoglobulin in blood plasma, produces angiotensin I. Angiotensin I is converted by angiotensin converting enzyme (ACE) to angiotensin II. The latter is an active pressor substance which has been implicated as the causative agent in various forms of hypertension in various mammalian species, e.g., rats, dogs, etc. The compounds of this invention intervene in the angiotensinogen → angiotensin I → angiotensin II sequence by inhibiting angiotensin converting enzyme and reducing or eliminating the formation of the pressor substance angiotensin II.

The inhibition of the angiotensin converting enzyme by compounds of formula I can be measured in vitro with isolated angiotensin converting enzyme from rabbit lungs following the procedure described by Cushman and Cheung [Biochem. Pharmacol., 20, 1637 (1971)], and with an excised smooth muscle assay [E. O'Keefe, et al., Federation Proc. 31, 511 (1972)] in which these compounds have been shown to be powerful inhibitors of the contractile activity of angiotensin I and potentiators of the contractile activity of bradykinin.

The administration of a composition containing one or a combination of compounds of formula I or physiologically acceptable salt thereof to the species of hypertensive mammal alleviates or reduces angiotensin dependent hypertension. A single dose, or preferably two to four divided daily doses, provided on the basis of about 5 to 1000 mg. per kilogram per day, preferably about 10 to 500 mg. per kilogram per day is appropriate to reduce blood pressure. The animal model experiments described by S. L. Engel, T. R. Schaeffer, M. H. Waugh and B. Rubin, Proc. Soc. Exp. Biol. Med. 143, 483 (1973) serve as a useful guide.

The substance is preferably administered orally, but parenteral routes such as subcutaneously, intramuscularly, intravenously or intraperitoneally can also be employed.

The compounds of this invention can be utilized to achieve the reduction of blood pressure by formulating in compositions such as tablets, capsules or elixirs for oral administration or in sterile solution or suspensions for parenteral administration. About 10 to 500 mg. of a compound or mixture of compounds of formula I or physiologically acceptable salt is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

The following examples are illustrative of the invention. All temperatures are in degrees celsius.

EXAMPLE 1

2-(Acetylthiomethyl)-3-(acetylthio)propanoic acid

A solution of 3.36 g. (40 mmoles) of thiolacetic acid in 40 ml. of N-potassium hydroxide is added dropwise to a solution of 2-bromomethyl-3-bromopropanoic acid in N potassium hydroxide (20 ml.). The mixture is stirred at room temperature overnight, acidified with concentrated hydrochloric acid and extracted with ethyl acetate. The organic layer is dried and concentrated in vacuo. The residue is converted into a dicyclohexylammonium salt (m.p. 116°–118°) and the salt converted back into the free acid, 2-(acetylthiomethyl)-3-(acetylthio)propanoic acid, by distribution between ethyl acetate and 10% potassium bisulfate.

EXAMPLE 2

1-[2-(Acetylthiomethyl)-3-(acetylthio)propanoyl]-L-proline tert-butyl ester 2-(Acetylthiomethyl)-3-(acetylthio)propanoic acid (2.36 g.) is added to a solution of L-proline tert. butyl ester (1.71 g.), hydroxybenzotriazole (1.35 g.) and dicyclohexylcarbodiimide (2.06 g.) in dichloromethane (15 ml.) chilled in an ice bath. The reaction mixture is stirred overnight at room temperature, the dicyclohexylurea is filtered off, and the filtrate is washed neutral. The organic layer is dried, and concentrated to dryness in vacuo to yield 1-[2-acetylthiomethyl)-3-(acetylthio)-propanoyl]-L-proline tert-butyl ester as a heavy oil (3.7 g.). Rf: 0.7 (silica gel-benzene, acetic acid 7:1).

EXAMPLE 3

1-[(2-Acetylthiomethyl)-3-(acetylthio)propanoyl]-L-proline (A) 1-[(2-Acetylthiomethyl)-3-(acetylthio)-propanoyl]-L-proline tert-butyl ester (2.7 g.) is dissolved in a mixture of trifluoroacetic acid and anisole and the mixture is stored at room temperature for one hour. The solvent is removed in vacuo and the residue is dissolved in saturated sodium bicarbonate solution. This aqueous solution is extracted with ethyl acetate, acidified with concentrated hydrochloric acid and reextracted with ethyl acetate. This second organic layer is dried and concentrated to dryness in vacuo. The residue is chromatographed on a column of silica gel with a mixture of benzene-acetic acid (7:1). The fractions containing the desired material are pooled and concentrated to dryness to yield 1-[(2-acetylthiomethyl)-3-(acethylthio)propanoyl]-L-proline as an oil (1.3 g.). Rf: 0.3 (silica gel: benzene-acetic acid 75:25).

(B) To a solution of L-proline (1.44 g.) and sodium carbonate (2.7 g.) in water (25 ml.) in an ice bath, 2-(acetylthiomethyl)-3-(acetylthio)propanoic acid chloride (3.9 g. — prepared from 2-(acetylthiomethyl)-3-(acetylthio)propanoic acid and thionyl chloride) is added and the mixture is vigorously stirred at room temperature for two hours. After extraction with ethyl acetate, the aqueous layer is acidified and extracted with ethyl acetate. The organic layer is dried and concentrated to dryness. The residue, 1-[(2-acetylthiomethyl)-3-(acetylthio)propanoyl]-L-proline is chromatographed as described in procedure (A) above.

EXAMPLE 4

1-(2-Mercaptomethyl-3-mercaptopropanoyl)-L-proline

1-[(2-Acetylthiomethyl-3-(acetylthio)propanoyl]-L-proline (1.2 g.) is dissolved in a mixture of water (12 ml.) and concentrated ammonia (12 ml.) under an atmosphere of argon. After twenty minutes, the mixture is acidified with concentrated hydrochloric acid. The crystalline precipitate 1-(2-mercaptomethyl-3-mercaptopropanoyl)-L-proline is filtered and dried, yield 0.63 g., m.p. 138°–140°.

EXAMPLE 5

2,3-(Diacetylthio)propanoic acid

By substituting 2,3-dibromopropanoic acid for the 2-bromomethyl-3-bromopropanoic acid in the procedure of Example 1,2,3-(diacetylthio)propanoic acid is obtained as an oil. Rf: 0.4 (silica gel:benzene-acetic acid 7:1).

EXAMPLE 6

1-[2,3-(Diacetylthio)propanoyl]-L-proline tert-butyl ester

By substituting 2,3-(diacetylthio)propanoic acid for the 2-(acetylthiomethyl)-3-(acetylthio)propanoic acid in the procedure of Example 2, 1-[2,3-(diacetylthio)-propanoyl]-L-proline tert-butyl ester is obtained as an oil. Rf: 0.5 (silica gel:chloroform-methane 98:2).

EXAMPLE 7

1-[2,3-(Diacetylthio)propanoyl]-L-proline

By substituting 1-[2,3-(diacetylthio)propanoyl]-L-proline tert-butyl ester for the 1-[(2-acetylthiomethyl)-3-acetylthiopropanoyl]-L-proline tert-butyl ester in the procedure of Example 3A, 1-[2,3-(diacetylthio)-propanoyl]-L-proline is obtained. Rf: 0.45 (silica gel: benzene: acetic acid, 75-25).

EXAMPLE 8

1-[2,3-Dimercaptopropanoyl]-L-proline

By substituting 1-[2,3-(diacetylthio)propanoyl]-L-proline for the 1-[(2-acetylthiomethyl-3-(acetylthio)-propanoyl]-L-proline in the procedure of Example 4, 1-[2,3-dimercaptopropanoyl]-L-proline is obtained. This product is isolated as an oil by extraction with ethyl acetate after acidification of the reaction mixture. Rf: 0.43 (silica gel-no indicator-benzene:acetic acid 75:25).

EXAMPLE 9

2-Bromo-3-(4-methoxybenzylmercapto)propanoic acid

By substituting 3-(4-methoxybenzyl)cysteine for the S-benzylcysteine in the procedure described by N. Izumiya (Chemical Abstracts, 47, 3236), 2-bromo-3-(4-methoxybenzylmercapto)propanoic acid is obtained.

EXAMPLE 10

3-(4-Methoxybenzylmercapto)-2-(methylthio)-propanoic acid

A solution of 2-bromo-3-(4-methoxybenzylmercapto)propanoic acid (15 g.), methylmercaptan (3 g.) and sodium hydroxide (4.6 g.) in 95% ethanol (25 ml.) is refluxed for twelve hours. The sodium bromide is filtered off and the filtrate is concentrated to dryness in vacuo. The residue is dissolved in water, acidified with concentrated hydrochloric acid and extracted with ethyl acetate. The organic layer is dried and concentrated to dryness to yield 3-(4-methoxybenzylmercapto)-2-(methylthio)propanoic acid.

EXAMPLE 11

1-[3-(4-Methoxybenzylmercapto)-2-(methylthio)-propanoyl]-L-proline tert-butyl ester By substituting 3-(4-methoxybenzylmercapto)-2-(methylthio)propanoic acid for the 2-(acetylthiomethyl)-3-(acetylthio)propanoic acid in the procedure of Example 2, 1-[3-(4-methoxybenzylmercapto)-2-(methylthio)-propanoyl]-L-proline tert-butyl ester is obtained.

EXAMPLE 12

1-[3-Mercapto-(2-methylthio)propanoyl]-L-proline

1-[3-(4-Methoxybenzylmercapto)-2-(methylthio)-propanoyl]-L-proline tert-butyl ester (0.5 g.) is dissolved in a mixture of dichloromethane (2 ml.) and anisole (1.1 ml.) under a blanket of argon in an ice bath. Trifluoromethanesulfonic acid (1 g.) is added and the mixture is stirred at room temperature for thirty minutes. The solvent is removed in vacuo and the residue is distributed between water and ethyl acetate. The organic layer is washed six times with water, dried and concentrated to dryness in vacuo to yield 1-[3-mercapto-2-(methylthio)propanoyl]-L-proline.

EXAMPLE 13

Ethyl-2-methylthiomethylacrylate

A solution of methylmercaptan (4.8 g.) and sodium (2.3 g.) in absolute ethanol (75 ml.) is added dropwise to a solution of ethyl-2-bromomethylacrylate (19.3 g.) in ethanol (25 ml.). After two hours, it is diluted with water (400 ml.) and extracted with methylene chloride. The organic layer is dried and concentrated to dryness in vacuo to yield ethyl-2-methylthiomethylacrylate.

EXAMPLE 14

(2-Methylthiomethyl)acrylic acid

Ethyl-2-methylthioacrylate (5 g.) is heated with 10% sulfuric acid (100 ml.) at 80° for one hour. After cooling, the aqueous phase is extracted with ethyl acetate to give (2-methylthiomethyl)acrylic acid.

EXAMPLE 15

3-(Acetylthio)-2-(methylthiomethyl)propanoic acid

A mixture of 2-(methylthiomethyl)acrylic acid (5.5 g.) and thiolacetic acid (5 ml.) is heated in the steam bath until disappearance of vinyl proton absorption in the nmr. The mixture is concentrated to remove the excess thiolacetic acid to obtain 3-(acetylthio)-2-(methylthiomethyl)propanoic acid.

EXAMPLE 16

1-[3-Acetylthio)-2-methylthiomethyl)propanoyl]-L-proline

To a solution of L-proline (1.44 g.) and sodium carbonate (2.7 g.) in water (25 ml.) in an ice bath, 3-(acetylthio)-2-(methylthiomethyl)propanoic acid chloride (prepared from the acid of Example 15 with thionyl chloride) (3.6 g.) is added, and the mixture is vigorously stirred at room temperature for two hours. After extraction with ethyl acetate, the aqueous layer is acidified and extracted with ethyl acetate. The organic layer is dried and concentrated to dryness in vacuo to give 1-[3-(acetylthio)-2-(methylthiomethyl)propanoyl]-L-proline.

EXAMPLE 17

1-[3-Mercapto-2-(methylthiomethyl)propanoyl]-L-proline

1-[3-(acetylthio)-2-(methylthiomethyl)propanoyl]-L-proline (1.2 g.) is dissolved in a mixture of water (12 ml.) and concentrated ammonia (12 ml.) under a blanket of argon. After twenty minutes, the reaction mixture is acidified and extracted with ethyl acetate. The organic layer is dried and concentrated to dryness to yield 1-([3-mercapto-2-(methylthiomethyl)propanoyl]-L-proline.

EXAMPLE 18

2-Acetoxymethyl-3-(acetylthio)propanoic acid (A) By substituting 2-(acetoxymethyl)acrylic acid [J. Org. Chem., 28, 2835 (1963)] for the 2-(methylthiomethyl)acrylic acid in the procedure of Example 15, 2-acetoxymethyl-3-(acetylthio)propanoic acid is obtained.

(B) By substituting 2-(hydroxymethyl)acrylic acid [J. Org. Chem., 28, 2835 (1963)] for the 2-(methylthiomethyl)acrylic acid in the procedure of Example 15, and then submitting the product to acetylation with acetic anhydride, 2-hydroxymethyl-3-(acetylthio)propanoic acid and 2-acetoxymethyl-3-(acetylthio)propanoic acid are obtained.

EXAMPLE 19

1-[2-(Acetoxymethyl)-3-(acetylthio)propanoyl]-L-proline

By substituting 2-(acetoxymethyl)-3-(acetylthio)propanoic acid for the 3-acetylthio-2-methylthiomethylpropanoic acid in the procedure of Example 16, 1-[2-(acetoxymethyl)-3-(acetylthio)propanoyl]-L-proline is obtained.

EXAMPLE 20

1-(2-Hydroxy-3-mercaptopropanoyl)-L-proline

1-[2-acetoxymethyl-3-(acetylthio)propanoyl]-L-proline (1.5 g.) is dissolved in a mixture of water (12 ml.) and concentrated ammonia (12 ml.) under a blanket of argon. After one hour, the reaction mixture is concentrated to ca. dryness, diluted with water and the solution applied to a column of cation exchange resin (Dowex 50) in the hydrogen cycle. The water eluate is concentrated to small volume and freeze dried to yield 1-(2-hydroxymethyl-3-mercaptopropanoyl)-L-proline.

EXAMPLE 21

2-Acetylthiomethyl-5-oxo-6-methylheptanoic acid

By substituting 2-methylene-5-oxo-6-methylheptanoic acid [Agr. Biol. Chem., 37, 2365, (1973)] for the (2-methylthiomethyl)acrylic acid in the procedure of Example 15, 2-acetylthiomethyl-5-oxo-6-methylheptanoic acid is obtained.

EXAMPLE 22

1-[2-(Acetylthiomethyl)-5-oxo-6-methylheptanoyl]-L-proline tert.butyl ester

By substituting 2-acetylthiomethyl-5-oxo-6-methylheptanoic acid for the 2-(acetylthiomethyl)-3-acetylthiopropanoic acid in the procedure of Example 2, 1-[2-acetylthiomethyl)-5-oxo-6-methylheptanoyl]-L-proline tert.butyl ester is obtained.

EXAMPLE 23

1-[2-(Acetylthiomethyl)-5-oxo-6-methylheptanoyl]-L-proline

By substituting 1-[2-(acetylthiomethyl)-5-oxo-6-methylheptanoyl]-L-proline tert.butyl ester for 1-[2-(acetylthiomethyl)-3-acetylthiopropanoyl]-L-proline tert.butyl ester in the procedure of Example 3, 1-[2-(acetylthiomethyl)-5-oxo-6-methylheptanoyl]-L-proline is obtained.

EXAMPLE 24

1-[2-(Acetylthiomethyl)-5-hydroxy-6-methylheptanoyl]-L-proline

1-[2-(acetylthiomethyl)-5-oxo-6-methylheptanoyl]-L-proline (1.5 g.) is dissolved in cold methanol (10 ml.) and sodium borohydride (0.12 g.) is added. After two hours the reaction mixture is diluted with water (100 ml.) acidified with concentrated hydrochloric acid and extracted with ethyl acetate. The organic layer is dried and concentrated to dryness in vacuo to give 1-[2-(acetylthiomethyl)-5-hydroxy-6-methylheptanoyl]-L-proline.

EXAMPLE 25

1-[2-Mercaptomethyl-5-hydroxy-6-methylheptanoyl]-L-proline

By substituting 1-[2-(acetylthiomethyl)-5-hydroxy-6-methylheptanoyl]-L-proline for the 1-[3-acetylthio-2-(methylthiomethyl)propanoyl]-L-proline in the procedure of Example 17, 1-[2-mercaptomethyl-5-hydroxy-6-methylheptanoyl]-L-proline is obtained.

EXAMPLE 26

1-[2-Benzoylthio-3-methoxybutanoyl]-L-proline

To a solution of L-proline (5.75 g.) in N sodium hydroxide (50 ml.) chilled in an ice bath, 2N sodium hydroxide (25 ml.) and 2-bromo-3-methoxybutyric acid chloride [obtained from 2-bromo-3-methoxybutyric acid [J. Am. Chem. Soc., 71, 1096, (1949)] and thionyl chloride] (10.7 g.) are added, with vigorous stirring. After three hours, thiobenzoic acid (7.5 g.) and potassium carbonate (4.8 g.) are added and the mixture is stirred at room temperature overnight. The reaction mixture is acidified and extracted with ethyl acetate. The organic layer is concentrated to dryness and the residue is chromatographed on a column of silica gel with benzene-acetic acid to yield 1-[2-benzoylthio-3-methoxybutanoyl]-L-proline.

EXAMPLE 27

1-[2-Mercapto-3-methoxybutanoyl]-L-proline

By substituting 1-[2-benzoylthio-3-methoxybutanoyl]-L-proline for the 1-[3-acetylthio-2-(methylthiomethyl)propanoyl]-L-proline in the procedure of Example 17, 1-[2-mercapto-3-methoxybutanoyl]-L-proline is obtained.

EXAMPLE 28

1-[2-Benzoylthio-3-(methylthio)propanoyl]-L-proline

By substituting 2-bromo-3-(methylthio)propanoic acid (Chemical Abstracts, 47, 3236) for the 2-bromo-3-methoxybutyric acid in the procedure of Example 26, 1-[2-benzoylthio-3-(methylthio)propanoyl]-L-proline is obtained.

EXAMPLE 29

1-[2-Mercapto-3-(methylthio)propanoyl]-L-proline

By substituting 1-[2-benzoylthio-3-(methylthio)propanoyl]-L-proline for the 1-[3-acetylthio-2-(methylthiomethyl)propanoyl]-L-proline in the procedure of Example 17, 1-[2-mercapto-3-(methylthio)propanoyl]-L-proline is obtained.

EXAMPLE 30

1,1-[Dithiobis[2-(methylthiomethyl)-3-propanoyl]]-bis-L-proline

1-[3-mercapto-2-(methylthiomethyl)propanoyl]-L-proline (2.0 g.) is dissolved in 40 ml. of 0.5 N sodium hydroxide, and an ethanolic solution of iodine is added until persistent yellow color, while keeping the pH between 5 and 7 by careful addition of N sodium hydroxide. The yellow color is discharged with a small amount of sodium thiosulfate, and after acidification with concentrated hydrochloric acid, the aqueous layer is extracted with ethyl acetate. The organic layer is dried and concentrated to dryness to yield 1,1'-[dithiobis[2-(methylthiomethyl)-3-propanoyl]]-bis-L-proline.

EXAMPLE 31

1,1'-[Dithiobis(2-hydroxymethyl-3-propanoyl)]-bis-L-proline

By substituting 1-(2-hydroxymethyl-3-mercaptopropanoyl)-L-proline for the 1-[3-mercapto-2-(methylthiomethyl)propanoyl]-L-proline in the procedure of Example 30, 1,1'-[dithiobis(2-hydroxymethyl-3-propanoyl)]-bis-L-proline is obtained.

EXAMPLE 32

1-[2-Mercaptomethyl-3-mercaptopropanoyl]-pipecolic acid

By substituting pipecolic acid tert.butyl ester for the L-proline tert.butyl ester in the procedure of Example 2, and then submitting the product to the procedures of Examples 3 and 4, 1-[2-(acetylthiomethyl)-3-(acetylthio)propanoyl]-pipecolic acid tert.butyl ester, 1-[(2-acetylthiomethyl)-3-(acetylthio)propanoyl]pipecolic acid and 1-[2-mercaptomethyl-3-mercaptopropanoyl]-pipecolic acid are obtained.

EXAMPLE 33

1-[2-Hydroxymethyl-3-mercaptopropanoyl]pipecolic acid

By substituting pipecolic acid for the L-proline in the procedure of Example 19, and then submitting the product to the procedure of Example 20, 1-[2-acetoxymethyl-3-(acetylthio)propanoyl]pipecolic acid and 1-[2-hydroxymethyl-3-mercaptopropanoyl]pipecolic acid are obtained.

EXAMPLE 34

N-[2-(Mercaptomethyl)-3-mercaptopropanoyl]-L-leucine

By substituting L-leucine for the L-proline in the procedure of Example 3B, and then submitting the product to the procedure of Example 4, 1-[(2-acetylthiomethyl)-3-acetylthiopropanoyl]-L-leucine and 1-[(2-mercaptomethyl)-3-mercaptopropanoyl]-L-leucine are obtained.

EXAMPLE 35

N-[2-(Mercaptomethyl)-3-mercaptopropanoyl]-L-phenylalanine

By substituting L-phenylalanine for the L-proline in the procedure of Example 3B, and then submitting the product to the procedure of Example 4, 1-[2-acetylthiomethyl)-3-acetylthiopropanoyl]-L-phenylalanine and 1-[2-(mercaptomethyl)-3-mercaptopropanoyl]-L-phenylalanine are obtained.

EXAMPLE 36

$N^\alpha$-[2-(Acetylthiomethyl)-3-(acetylthio)propanoyl]-L-arginine

L-Arginine (8.7 g.) is dissolved in aqueous N sodium hydroxide (50 ml.) and the solution is chilled in an ice bath with stirring. 2N sodium hydroxide (25 ml.) and 2-(acetylthiomethyl)-3-acetylthiopropanoic acid chloride (15.6 g.) are added in that order, and the mixture is removed from the ice bath and stirred at room temperature for two hours. The reaction mixture is extracted with ethyl acetate and the aqueous layer is applied to a cation exchange column (Dowex 50) in the hydrogen cycle. After washing with water to elute acidic material, the $N^\alpha$-[2-(acetylthiomethyl)-3-(acetylthio)-propanoyl]-L-arginine is eluted with a pyridine-acetic acid buffer at pH 6.5.

EXAMPLE 37

$N^\alpha$-[2-Mercaptomethyl)-3-mercaptopropanyl]-L-arginine $N^\alpha$-[2-(acetylthiomethyl)-3-(acetylthio)propanoyl]-L-arginine (1 g.) is dissolved in a mixture of water (5 ml.) and concentrated ammonia (5 ml.). After thirty minutes, the solution is concentrated to dryness and the residue is applied to a column of Dowex 50 in the hydrogen cycle. After washing with water to remove acidic material, the $N^\alpha$-[2-mercaptomethyl-3-mercaptopropanoyl]-L-arginine is eluted with a pyridine-acetic acid buffer at pH 6.5.

EXAMPLE 38

$N^\alpha$-[2-(Acetylthiomethyl)-3-(acetylthio)propanoyl]-$N^\epsilon$-tert. butyloxycarbonyl-L-lysine tert.butyl ester By substituting $N^\epsilon$-tert.butyloxycarbonyl-L-lysine tert.butyl ester for the L-proline tert.butyl ester in the procedure of Example 2, $N^\alpha$-[2-(acetylthiomethyl)-3-(acetylthio)propanoyl]-$N^\epsilon$-tert.butyloxycarbonyl-L-lysine tert.butyl ester is obtained.

EXAMPLE 39

$N^\alpha$-[2-(Acetylthiomethyl)-3-(acetylthio)propanoyl]-L-lysine $N^\alpha$-[2-(acetylthiomethyl)-3-(acetylthio)propanoyl]-$N^\epsilon$-tert.butyloxycarbonyl-L-lysine tert.butyl ester (3 g.) is dissolved in a mixture of trifluoroacetic acid and anisole, and the mixture is stored at room temperature for one hour. The trifluoroacetic acid is removed in vacuo, the residue is distributed between ether and water and the aqueous layer is applied to a column of Dowex 50. After washing the acidic material with water, the $N^\alpha$-[2-(acetylthiomethyl)-3-(acetylthio)propanoyl]-L-lysine is eluted with a buffer of pyridine-acetic acid at pH 6.5.

EXAMPLE 40

$N^\alpha$-[2-Mercaptomethyl-3-mercaptopropanoyl]-L-lysine

By substituting N-[2-(acetylthiomethyl)-3-(acetylthio)propanoyl]-L-lysine for $N^\alpha$-[2-(acetylthiomethyl)-3-(acetylthio)propanoyl]-L-arginine in the procedure of Example 37, $N^\alpha$-[2-mercaptomethyl-3-mercaptopropanoyl]-L-lysine is obtained.

EXAMPLE 41

N-[2-(Mercaptomethyl)-3-mercaptopropanoyl]glycine

By substituting glycine for the L-proline in the procedure of Example 3B and then submitting the product to the procedure of Example 4, N-[2-(acetylthiomethyl)-3-(acetylthio)propanoyl]glycine and N-[2-(mercaptomethyl)-3-mercaptopropanoyl]glycine are obtained.

EXAMPLE 42

N-[2-(Mercaptomethyl)-3-mercaptopropanoyl]-L-glutamine

By substituting L-glutamine for the L-proline in the procedure of Example 3B, and then submitting the product to the procedure of Example 4, N-[2-(acetylthiomethyl)-3-(acetylthio)propanoyl]-L-glutamine and 1-[2-(mercaptomethyl)-3-mercaptopropanoyl]-L-glutamine are obtained.

EXAMPLE 43

N-[2-(Mercaptomethyl)-3-mercaptopropanoyl]-L-threonine

By substituting L-threonine for the L-proline in the procedure of Example 3B, and then submitting the product to the procedure of Example 4, N-[2-(acetylthiomethyl)-3-(acetylthio)propanoyl]-L-threonine and 1-[2-(mercaptomethyl)-3-mercaptopropanoyl]-L-threonine are obtained.

EXAMPLE 44

1-[2-(Mercaptomethyl)-3-mercaptopropanoyl]-4-hydroxy-L-proline

By substituting 4-hydroxy-L-proline for the L-proline in the procedure of Example 3B, and then submitting the product to the procedure of Example 4, 1-[2-(acetylthiomethyl)-3-acetylthio)propanoyl]-4-hydroxy-L-proline and 1-[2-(mercaptomethyl)-3-mercaptopropanoyl]-4-hydroxy-L-proline are obtained.

EXAMPLE 45

$N^\alpha$-[2-(Mercaptomethyl)-3-mercaptopropanoyl]-L-histidine

By substituting L-histidine for the L-arginine in the procedure of Example 36 and then submitting the product to the procedure of Example 37, $N^\alpha$-[2-(mercaptomethyl)-3-mercaptopropanoyl]-L-histidine is obtained.

EXAMPLE 46

N-[2-(Mercaptomethyl)-3-mercaptopropanoyl]-L-tryptophane

By substituting L-tryptophane for the L-proline in the procedure of Example 3B and then submitting the product to the procedure of Example 4, N-[2-(acetylthiomethyl)-3-(acetylthio)propanoyl]-L-tryptophane and N-[2-(mercaptomethyl)-3-mercaptopropanoyl]-L-tryptophane are obtained.

EXAMPLE 47

$N^\alpha$-[2-(Hydroxymethyl)-3-mercaptopropanoyl]-L-arginine

By substituting 2-(acetoxymethyl)-3-(acetylthio)propanoic acid chloride for the 2-(acetylthiomethyl)-3-(acetylthio)propanoic acid chloride in the procedure of Example 36, and then submitting the product to the procedure of Example 37, $N^\alpha$-[2-(acetoxymethyl)-3-(acetylthio)propanoyl]-L-arginine, and $N^\alpha$-[2-(hydroxymethyl)-3-mercaptopropanoyl]-L-arginine are obtained.

EXAMPLE 48

$N^\alpha$-[2-Hydroxymethyl)-3-mercaptopropanoyl]-L-lysine

By substituting 2-(acetoxymethyl)-3-(acetylthio)propanoic acid for the 2-(acetylthiomethyl)-3-(acetylthio)propanoic acid in the procedure of Example 38, and then submitting the product to the procedures of Examples 39 and 40, $N^\alpha$-[2-(acetoxymethyl)-3-(acetylthio)propanoyl]-$N^\epsilon$-tert.butyloxycarbonyl-L-lysine tert.butyl ester, $N^\alpha$-[2-(acetoxymethyl)-3-(acetylthio)propanoyl]-L-lysine, and $N^\alpha$-[2-(hydroxymethyl)-3-mercaptopropanoyl]-L-lysine are obtained.

EXAMPLE 49

N-[2-(Hydroxymethyl)-3-mercaptopropanoyl]glycine

By substituting glycine for the L-proline in the procedure of Example 19, and then submitting the product to the procedure of Example 20, N-[2-(acetoxymethyl)-3-(acetylthio)propanoyl]glycine and N-[2-(hydroxymethyl)-3-mercaptopropanoyl]glycine are obtained.

EXAMPLE 50

N-[2-(Hydroxymethyl)-3-mercaptopropanoyl]-L-leucine

By substituting L-leucine for the L-proline in the procedure of Example 19, and then submitting the product to the procedure of Example 20, N-[2-(acetoxymethyl)-3-(acetylthio)propanoyl]-L-leucine, and N-[2-(hydroxymethyl)-3-mercaptopropanoyl]-L-leucine are obtained.

EXAMPLE 51

N-[2-(Hydroxymethyl-3-mercaptopropanoyl]-L-phenylalanine

By substituting L-phenylalanine for the L-proline in the procedure of Example 19, and then submitting the product to the procedure of Example 20, N-[2-(acetoxymethyl)-3-(acetylthio)propanoyl]-L-phenylalanine and N-[2-(hydroxymethyl)-3-mercaptopropanoyl]-L-phenylalanine are obtained.

EXAMPLE 52

N-[2-(Hydroxymethyl)-3-mercaptopropanoyl]-L-serine

By substituting L-serine for the L-proline in the procedure of Example 19, and then submitting the product to the procedure of Example 20, N-[2-(acetoxymethyl)-3-(acetylthio)propanoyl]-L-serine and N-[2-(hydroxymethyl)-3-mercaptopropanoyl]-L-serine are obtained.

EXAMPLE 53

N-[2-(Hydroxymethyl)-3-mercaptopropanoyl]-L-cysteine

By substituting S-ethylcarbamoyl-L-cysteine for the L-proline in the procedure of Example 19, and then submitting the product to the procedure of Example 20, N-[2-acetoxymethyl)-3-(acetylthio)propanoyl]-S-ethylcarbamoyl-L-cysteine and N-[2-(hydroxymethyl)-3-mercaptopropanoyl]-L-cysteine are obtained.

EXAMPLE 54

N-[2-(Hydroxymethyl)-3-mercaptopropanoyl]-L-methionine

By substituting L-methionine for the L-proline in the procedure of Example 19, and then submitting the product to the procedure of Example 20, N-[2-(acetoxymethyl)-3-(acetylthio)propanoyl]-L-methionine and N-[2-(hydroxymethyl)-3-mercaptopropanoyl]-L-methionine are obtained.

EXAMPLE 55

N-[2-(Hydroxymethyl)-3-mercaptopropanoyl]-L-asparagine

By substituting L-asparagine for the L-proline in the procedure of Example 19, and then submitting the product to the procedure of Example 20, N-[2-(acetoxymethyl)-3-(acetylthio)propanoyl]-L-asparagine and N-[2-(hydroxymethyl)-3-mercaptopropanoyl]-L-asparagine are obtained.

EXAMPLE 56

N-[2-(Hydroxymethyl)-3-mercaptopropanoyl]-L-glutamic acid

By substituting L-glutamic acid for the L-proline in the procedure of Example 19, and then submitting the product to the procedure of Example 20, N-[2-(acetoxymethyl)-3-(acetylthio)propanoyl]-L-glutamic acid and N-[2-(hydroxymethyl)-3-mercaptopropanoyl]-L-glutamic acid are obtained.

EXAMPLE 57

N-[2-(Hydroxymethyl)-3-mercaptopropanoyl]-L-tyrosine

By substituting L-tyrosine for the L-proline in the procedure of Example 19, then submitting the product to the procedure of Example 20, N-[2-(acetoxymethyl)-3-(acetylthiomethyl)propanoyl]-L-tyrosine, and N-[2-(hydroxymethyl)-3-(mercapto)propanoyl]-L-tyrosine are obtained.

EXAMPLE 58

N,N'-[Dithiobis(2-hydroxymethyl-3-propanoyl)]-bis-L-phenylalanine

By substituting N-[2-(hydroxymethyl)-3-mercaptopropanoyl]-L-phenylalanine for the 1-[3-mercapto-2-methylthiopropanoyl]-L-proline in the procedure of Example 30 N,N'-[dithiobis(2-hydroxymethyl-3-propanoyl]-bis-L-phenylalanine is obtained.

EXAMPLE 59

2-Acetoxy-3-acetylthiopropanoic acid

By substituting 2-acetoxyacrylic acid for the 2-(methylthiomethyl)acrylic acid in the procedure of Example 15, 2-acetoxy-3-acetylthiopropanoic acid is obtained.

EXAMPLE 60

$N^\alpha$-(2-Hydroxy-3-mercaptopropanoyl)-L-lysine

By substituting 2-acetoxy-3-(acetylthio)propanoic acid for the 2-(acetylthiomethyl)-3-(acetylthio)propanoic acid in the procedure of Example 38 and then submitting the product to the procedures of Examples 39 and 40, $N^\alpha$-[2-acetoxy-3-(acetylthio)propanoyl]-$N^\epsilon$-tert.butyloxycarbonyl-L-lysine tert.butyl ester, $N^\alpha$-[2-acetoxy-3-(acetylthio)propanoyl]-L-lysine and $N^\alpha$-(2-hydroxy-3-mercaptopropanoyl)-L-lysine are obtained.

EXAMPLE 61

1-[(1,2-Dithiolane-4-yl)carbonyl]-L-proline

By substituting 1,2-dithiolane-4-carboxylic acid for the 2-(acetylthiomethyl)-3-acetylthiopropanoic acid in the procedure of Example 2 and then submitting the product to the process of Example 3, 1-[(1,2-dithiolane-4-yl)carbonyl]-L-proline tert.butyl ester and 1-[(1,2-dithiolane-4-yl)carbonyl]-L-proline are obtained.

EXAMPLE 62

N-[2-(Hydroxymethyl)-3-mercaptopropanoyl]-N-methyl-L-phenylalanine

By substituting N-methyl-L-phenylalanine for the L-proline in the procedure of Example 19 and then submitting the product to the procedure of Example 20, N-[2-(acetoxymethyl)-3-(acetylthio)propanoyl]-N-methyl-L-phenylalanine and N-[2-(hydroxymethyl)-3-mercaptopropanoyl]-N-methyl-L-phenylalanine are obtained.

The racemic forms of the final products in each of the foregoing examples are produced by utilizing the DL-form of the starting amino acid instead of the L-form.

Similarly the D-form of the final products in each of the foregoing examples is produced by utilizing the D-form of the starting amino acid instead of the L-form.

EXAMPLE 63

1000 tablets each containing 100 mg. of 1-(2-mercaptomethyl-3-mercaptopropanoyl)-L-proline are produced from the following ingredients:

| | |
|---|---|
| 1-(2-mercaptomethyl-3-mercapto-propanoyl)-L-Proline | 100 g. |
| Corn starch | 50 g. |
| Gelatin | 7.5 g. |
| Avicel (microcrystalline cellulose) | 25 g. |
| Magnesium stearate | 2.5 g. |

The 1-(2-mercaptomethyl-3-mercaptopropanoyl)-L-proline and corn starch are admixed with an aqueous solution of the gelatin. The mixture is dried and ground to a fine powder. The Avicel and then the magnesium stearate are admixed with the granulation. This is then compressed in a tablet to form 1000 tablets each containing 100 g. of active ingredient.

EXAMPLE 64

Two piece #1 gelatin capsules each containing 250 mg. of 1-[2,3-dimercaptopropanoyl]-L-proline are filled with a mixture of the following ingredients:

| | |
|---|---|
| 1-(2,3-dimercaptopropanoyl]-L-proline | 250 mg. |
| Magnesium stearate | 7 mg. |
| USP Lactose | 193 mg. |

EXAMPLE 65

By substituting 1-[2-mercaptomethyl-3-mercaptopropanoyl]-pipecolic acid for the 1-(2-mercaptomethyl)-3-mercaptopropanoyl)-L-proline in Example 63, 1000 tablets each containing 100 mg. of the former are obtained.

What is claimed is:

1. A compound of the formula

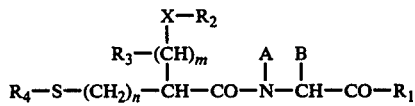

and salts thereof, wherein
$R_1$ is hydroxy or lower alkoxy;
$R_2$ is hydroge, lower alkyl or lower alkanoyl;
$R_3$ is hydrogen or lower alkyl;
$R_4$ is hydrogen, lower alkanoyl, benzoyl or

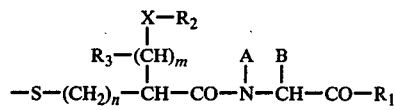

A is hydrogen, lower alkyl or hydroxy-lower alkylene;
B is phenyl, phenyl-lower alkylene, or hydroxyphenyl-lower alkylene;
X is oxygen or sulfur;
m is 0, 1, 2, 3 or 4; and
n is 0 or 1.

2. A compound as in claim 1 wherein

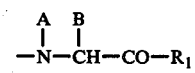

is the radical of phenyl-alanine, tyrosine, phenylglycine or N-methylphenylalanine.

3. A compound as in claim 1 wherein $R_1$ is hydroxy; $R_2$ is hydrogen, lower alkyl or lower alkanoyl; $R_3$ is hydrogen or lower alkyl; $R_4$ is hydrogen, lower alkanoyl or benzoyl; X is oxygen or sulfur; A is hydrogen; B is phenyl-lower alkylene; m is 0 or 1 and n is 0 or 1.

4. A compound as in claim 1 wherein $R_4$ is

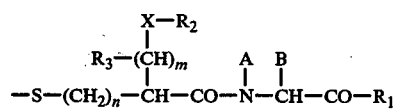

5. A compound as in claim 1 wherein X is oxygen.
6. A compound as in claim 1 wherein X is sulfur.
7. A compound as in claim 1 wherein $R_1$ is hydroxy; A, $R_2$, $R_3$ and $R_4$ each is hydrogen; B is phenylmethyl; X is sulfur; and m and n each is 1.
8. A compound as in claim 1 wherein $R_1$ is hydroxy; A, $R_2$, $R_3$ and $R_4$ each is hydrogen; B is phenylmethyl; X is oxygen; and m and n each is 1.
9. A compound as in claim 1 wherein $R_1$ is hydroxy; A, $R_2$, $R_3$ and $R_4$ each is hydrogen; B is (4-hydroxyphenyl)methyl; X is oxygen; and m and n each is 1.
10. A compound as in claim 4 wherein each $R_1$ is hydroxy; each A, $R_2$ and $R_3$ is hydrogen; each B is phenylmethyl; each X is oxygen; and each m and n is 1.
11. A compound as in claim 1 wherein $R_1$ is hydroxy; $R_2$, $R_3$ and $R_4$ each is hydrogen; A is methyl; B is phenylmethyl; X is oxygen; and m and n each is 1.

* * * * *